United States Patent
Sasaya

(10) Patent No.: US 9,959,638 B2
(45) Date of Patent: May 1, 2018

(54) X-RAY CT APPARATUS AND DATA COMPRESSION/RESTORATION METHOD

(71) Applicant: TOSHIBA MEDICAL SYSTEMS CORPORATION, Otawara-Shi (JP)

(72) Inventor: Tomotaka Sasaya, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 88 days.

(21) Appl. No.: 15/062,821

(22) Filed: Mar. 7, 2016

(65) Prior Publication Data

US 2016/0267653 A1 Sep. 15, 2016

(30) Foreign Application Priority Data

Mar. 12, 2015 (JP) ................................. 2015-049290
Feb. 16, 2016 (JP) ................................. 2016-026693

(51) Int. Cl.
*G06K 9/00* (2006.01)
*G06T 11/00* (2006.01)
(Continued)

(52) U.S. Cl.
CPC ............ *G06T 11/003* (2013.01); *A61B 6/032* (2013.01); *A61B 6/5205* (2013.01); *A61B 6/06* (2013.01)

(58) Field of Classification Search
CPC ......... A61B 6/032; A61B 6/06; A61B 6/5205; G06T 11/003; G06T 9/00; H04N 19/103; H04N 19/146; H04N 19/15; H04N 19/169; H04N 19/182; H04N 19/50; H04N 1/64; H04N 3/1562
See application file for complete search history.

(56) References Cited

U.S. PATENT DOCUMENTS

2003/0021456 A1  1/2003  Inoue
2003/0072419 A1*  4/2003  Bruder ................... A61B 6/032
                                                          378/210
(Continued)

FOREIGN PATENT DOCUMENTS

JP  2000-316134  11/2000
JP  2002-359786  12/2002
(Continued)

*Primary Examiner* — Bhavesh Mehta
*Assistant Examiner* — Ian Lemieux
(74) *Attorney, Agent, or Firm* — Oblon, McClelland, Maier & Neustadt, L.L.P.

(57) ABSTRACT

In one embodiment, an X-ray CT apparatus includes an X-ray tube that radiates, an X-ray, a detector that outputs a plurality of pieces of pre-compression data on a basis of the X-ray first processing circuitry and second processing circuitry. The first processing circuitry groups the plurality of pieces of pre-compression data to generate grouped data corresponding to the pre-compression data in each group, and generates data for restoration for restoring the pre-compression data, wherein the first processing circuitry transmits the grouped data and the data for restoration to the second processing circuitry. And the second processing circuitry selects any of a first reconstruction mode in which image reconstruction is performed based on the plurality of pieces of pre-compression data; and a second reconstruction mode in which image reconstruction is performed based on the data for restoration, and generates an image, and in a case of performing image reconstruction in the first reconstruction mode, the second processing circuitry restores the pre-compression data based on the grouped data and the data for restoration.

11 Claims, 12 Drawing Sheets

(51) Int. Cl.
    *A61B 6/03*     (2006.01)
    *A61B 6/00*     (2006.01)
    *A61B 6/06*     (2006.01)

(56) References Cited

U.S. PATENT DOCUMENTS

| | | | | |
|---|---|---|---|---|
| 2003/0228041 | A1* | 12/2003 | Bae | G06T 9/007 |
| | | | | 382/131 |
| 2006/0116567 | A1* | 6/2006 | Nilsen | A61B 6/032 |
| | | | | 600/407 |
| 2009/0169119 | A1* | 7/2009 | Wegener | H04N 19/124 |
| | | | | 382/232 |
| 2010/0128998 | A1* | 5/2010 | Wegener | G06T 9/00 |
| | | | | 382/248 |
| 2011/0150171 | A1* | 6/2011 | Breuer | A61B 6/56 |
| | | | | 378/4 |
| 2012/0237101 | A1* | 9/2012 | Kaempfer | A61B 6/032 |
| | | | | 382/131 |
| 2013/0216018 | A1* | 8/2013 | Nakai | A61B 6/032 |
| | | | | 378/4 |
| 2013/0251257 | A1 | 9/2013 | Ohnishi et al. | |
| 2013/0301890 | A1* | 11/2013 | Kaempfer | H04N 19/172 |
| | | | | 382/131 |
| 2015/0036907 | A1* | 2/2015 | Seong | G06T 3/4053 |
| | | | | 382/131 |

FOREIGN PATENT DOCUMENTS

| | | |
|---|---|---|
| JP | 2012-114876 | 6/2012 |
| JP | 2013-9907 | 1/2013 |

\* cited by examiner

X-RAY CT APPARATUS AND DATA COMPRESSION/RESTORATION METHOD

CROSS-REFERENCE TO RELATED APPLICATION

This application is based upon and claims the benefit of priority from Japanese Patent Application No. 2015-049290, filed on Mar. 12, 2015, and claims the benefit of priority from Japanese Patent Application No. 2016-026693, filed on Feb. 16, 2016, the entire contents of all of which are incorporated herein by reference.

FIELD

Embodiments described herein relate generally to a x-ray CT apparatus and data compression/restoration method.

BACKGROUND

A high-definition detector has been developed in recent years. A larger number of X-ray detecting elements can be mounted in the same area on the high-definition detector, because a size of each X-ray detecting element is smaller than that of an X-ray detector of a normal X-ray CT apparatus. In an X-ray CT apparatus including such a high-definition detector (hereinafter, referred to as the high-definition X-ray CT apparatus), the number of X-ray detecting elements is larger than that of the normal X-ray CT apparatus, and hence data volume acquired by the high-definition X-ray CT apparatus is larger accordingly.

Consequently, it is conceivable to compress raw data acquired by the high-definition X-ray CT apparatus (hereinafter, referred to as the high-definition data). In a case of generating a reconstruction image with an image quality equivalent to that of an image acquired by the normal X-ray CT apparatus, it is necessary to restore the original high-definition data. In such a case, extra time is necessary for the restoration of the original high-definition data, and the time required for a reconstruction process is longer as a whole.

DETAILED DESCRIPTION

Hereinafter, an X-ray CT apparatus and a data compression/restoration method of each embodiment of the present invention are described with reference to the attached drawings.

In one embodiment, an X-ray CT apparatus includes an X-ray tube that radiates, an X-ray, a detector that outputs a plurality of pieces of pre-compression data on a basis of the X-ray first processing circuitry and second processing circuitry. The first processing circuitry groups the plurality of pieces of pre-compression data to generate grouped data corresponding to the pre-compression data in each group, and generates data for restoration for restoring the pre-compression data, wherein the first processing circuitry transmits the grouped data and the data for restoration to the second processing circuitry. And the second processing circuitry selects any of a first reconstruction mode in which image reconstruction is performed based on the plurality of pieces of pre-compression data; and a second reconstruction mode in which image reconstruction is performed based on the data for restoration, and generates an image, and in a case of performing image reconstruction in the first reconstruction mode, the second processing circuitry restores the pre-compression data based on the grouped data and the data for restoration.

First Embodiment

Figure 1:
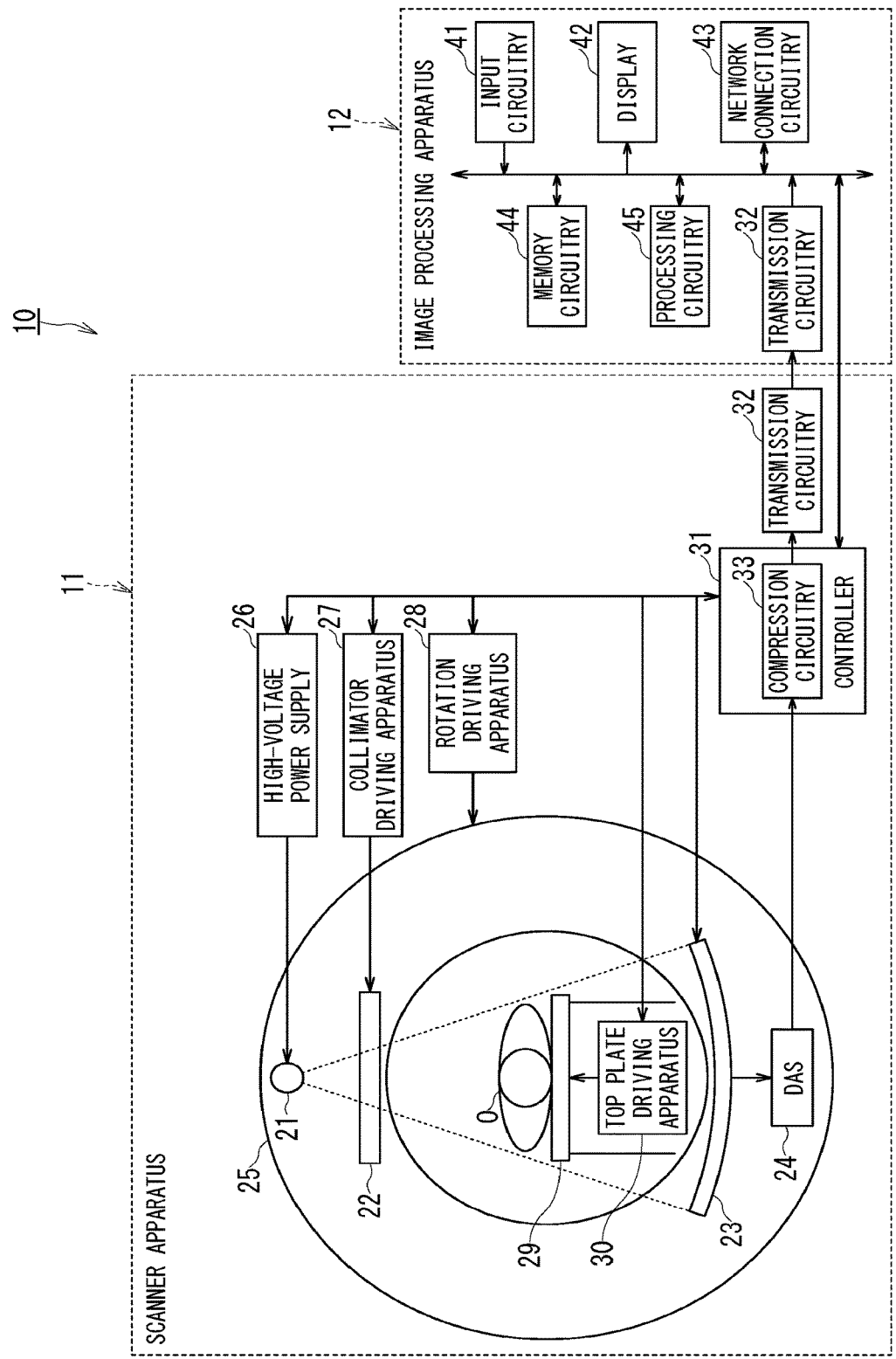
FIG. 1 is a conceptual configuration diagram illustrating an example of an X-ray CT apparatus according to the first embodiment.

FIG. 1 is a conceptual configuration diagram illustrating an example of an X-ray CT apparatus according to the first embodiment. As illustrated in FIG. 1, an X-ray CT apparatus 10 includes an scanner apparatus 11 and an image processing apparatus 12. The scanner apparatus 11 of the X-ray CT apparatus 10 is normally installed in an examination room, and generates projection data of X-rays concerning a site of an object O (patient). The image processing apparatus 12 is normally installed in a control room adjacent to the examination room, and, for example, performs a correction process and other processes on the projection data and then generates and displays a reconstruction image.

The scanner apparatus 11 of the X-ray CT apparatus 10 includes an X-ray tube 21, a collimator 22, an X-ray detector 23, a data acquisition system (DAS) 24, a rotating frame 25, a high-voltage power supply 26, a collimator driving apparatus 27, a rotation driving apparatus 28, a top plate 29, a top plate driving apparatus 30, a controller 31, and transmission circuitry 32. Here, for example, the controller 31 and the transmission circuitry 32 are provided to a frame apparatus including the X-ray tube 21, the collimator 22, the X-ray detector 23, the DAS 24, the rotating frame 25, the high-voltage power supply 26, the collimator driving apparatus 27, and the rotation driving apparatus 28.

Voltage (hereinafter, referred to as tube voltage) is applied to the X-ray tube 21 by the high-voltage power supply 26, whereby the X-ray tube 21 generates an X-ray. The X-ray generated by the X-ray tube 21 is radiated as a fan beam X-ray or a cone beam X-ray toward the object O.

The collimator 22 is controlled by the controller 31 via the collimator driving apparatus 27 to adjust a radiation range in a slice direction, of the X-ray radiated from the X-ray tube 21.

The X-ray detector 23 is configured using a plurality of X-ray detecting elements (charge accumulating elements). Each X-ray detecting element detects the X-ray radiated from the X-ray tube 21. The X-ray tube 21 and the X-ray detector 23 are supported by the rotating frame 25 so as to be opposed to each other with the object O placed on the top plate 29 being interposed therebetween.

For example, a so-called two-dimensional array (multi-slice) detector in which X-ray detecting elements having a plurality of channels in a channel (CH) direction are arranged in a plurality of lines in the slice direction may be used as the X-ray detector 23. The X-ray detector 23 of the present embodiment includes a high-definition detector whose X-ray detecting elements are smaller than those of a conventional X-ray detector. The X-ray detector 23 of the present embodiment includes, for example, larger numbers of X-ray detecting elements in the CH direction and the slice direction than those of the conventional X-ray detector, and thus can acquire an image with higher resolution in the same detection area.

The DAS 24 amplifies projection data of the X-ray detected by each X-ray detecting element constituting the X-ray detector 23, converts the projection data into a digital signal, and outputs the resultant projection data. The projection data outputted from the DAS 24 is transferred to compression circuitry 33 of the controller 31. From the DAS 24 to the compression circuitry 33, the projection data may be transferred for each slice and may be transferred for each projection angle (view). A method of transferring projection data for each slice is referred to as a collective transfer process, and a method of transferring projection data for each view is referred to as a sequential transfer process. The compression circuitry 33 performs a predetermined compression process on the projection data outputted from the DAS 24 to reduce the amount of data. The compression process performed by the compression circuitry 33 is specifically described later. Projection data before compression to be transferred to the compression circuitry 33 is hereinafter referred to as pre-compression data. The data whose amount has been reduced by the compression circuitry 33 is transmitted to the image processing apparatus 12 via the transmission circuitry 32.

The rotating frame 25 integrally holds the X-ray tube 21, the collimator 22, the X-ray detector 23, and the DAS 24. The rotating frame 25 is controlled by the controller 31 via the rotation driving apparatus 28 to rotate, whereby the X-ray tube 21, the collimator 22, the X-ray detector 23, and the DAS 24 integrally rotate around the object O.

The high-voltage power supply 26 is controlled by the controller 31 to supply electric power necessary for X-ray radiation to the X-ray tube 21.

The collimator driving apparatus 27 is controlled by the controller 31 to adjust an aperture of the collimator 22 and thus adjust the X-ray radiation range in the slice direction.

The rotation driving apparatus 28 is controlled by the controller 31 to rotate the rotating frame 25 around an opening portion of the rotating frame 25.

The object O can be placed on the top plate 29. The top plate driving apparatus 30 is controlled by the controller 31 to move the top plate 29 upward/downward. The top plate driving apparatus 30 is controlled by the controller 31 to transport the top plate 29 to an X-ray radiation field in the opening portion of a central portion of the rotating frame 25.

The controller 31 is configured using a processor and memory media typified by a RAM and a ROM, and controls the X-ray detector 23, the DAS 24, the high-voltage power supply 26, the collimator driving apparatus 27, the rotation driving apparatus 28, and the top plate driving apparatus 30 to execute scanning, in accordance with programs stored in the memory media. The compression circuitry 33 of the controller 31 is also processing circuitry that executes the compression process to be described later in accordance with programs stored in the memory media. The RAM of the controller 31 provides a work area for temporarily storing programs and data executed by the processor. The memory media typified by the ROM of the controller 31 store an activation program of the scanner apparatus 11, a control program of the scanner apparatus 11, and various pieces of data necessary to execute these programs.

The memory media typified by the RAM and the ROM of the controller 31 may include memory media readable by the processor, such as a magnetic or optical memory medium and a semiconductor memory, and the entirety or a part of the programs and the data in the memory media may be downloaded via an electronic network.

The image processing apparatus 12 of the X-ray CT apparatus 10 is configured using, for example, a personal computer, and can transmit/receive data to/from a network such as a hospital backbone local area network (LAN).

As illustrated in FIG. 1, the image processing apparatus 12 includes input circuitry 41, a display 42, network connection circuitry 43, memory circuitry 44, transmission circuitry 32, and processing circuitry 45.

The input circuitry 41 is configured using, for example, general input apparatuses such as a keyboard, a trackball, a touch panel, and a numeric keypad, and outputs an operation input signal corresponding to an operation by a user, to the processing circuitry 45. For example, if the user sets a scan plan via the input circuitry 41, the processing circuitry 45 including a processor gives the controller 31 an instruction for specifying, for example, X-ray radiation timing, an X-ray radiation period, and tube current and tube voltage to be applied to the X-ray tube 21, on a basis of the scan plan. The controller 31 instructs the high-voltage power supply 26 to supply electric power to the X-ray tube 21 using the tube current and the tube voltage specified by the processing circuitry 45, at the radiation timing and in the radiation period specified by the processing circuitry 45. The processing circuitry 45 executes programs stored in the memory circuitry 44 to thereby perform a restoration process and a reconstruction process to be described later.

The display 42 is configured using, for example, general display/output apparatuses such as a liquid crystal display and an organic light emitting diode (OLED) display, and displays various images such as a reconstruction image in accordance with control by the processing circuitry 45.

Various protocols for information communication respectively corresponding to network forms are implemented on the network connection circuitry 43. The network connection circuitry 43 connects the image processing apparatus 12 to other electrical equipment such as an image server, in accordance with the various protocols. For example, electrical connection via an electronic network can be applied to this connection.

The electronic network means overall information and communication networks using telecommunication technology, and includes a telephone communication network, an optical fiber communication network, a cable communication network, and a satellite communication network as well as wireless/wired LAN such as a hospital backbone LAN and the Internet.

The memory circuitry 44 includes memory media readable/writable by the processor of the processing circuitry 45, such as a magnetic or optical memory medium and a semiconductor memory. Although one memory circuitry 44 is illustrated in the example of FIG. 1, two memory circuitries 44 may be provided, and one memory circuitry 44 may be virtually divided into two regions for use. Moreover, an apparatus constituting the memory circuitry 44 may be multiplexed, and may be configured using redundant arrays of inexpensive disks (RAID) in which a plurality of hard disks are virtually used as one hard disk.

The entirety or a part of the programs and the data in the memory circuitry 44 may be downloaded via an electronic network.

Figure 2:
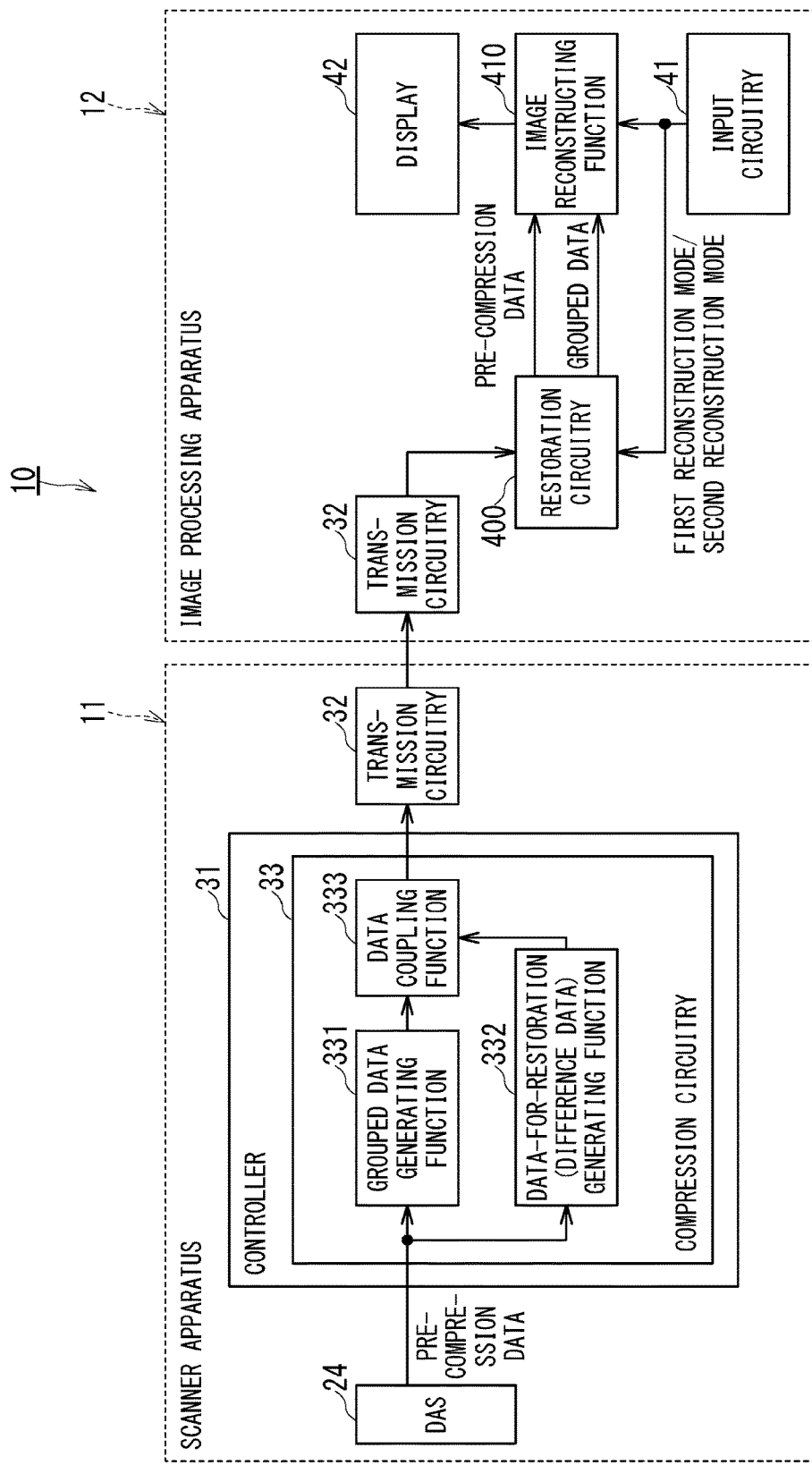
FIG. 2 is a functional block diagram illustrating a functional configuration example of the X-ray CT apparatus according to the first embodiment.

FIG. 2 is a functional block diagram illustrating a functional configuration example of the X-ray CT apparatus 10 according to the first embodiment. As illustrated in FIG. 2, the compression circuitry 33 of the scanner apparatus 11 includes a grouped data generating function 331, a data-for-restoration (difference data) generating function 332, and a data coupling function 333. The compression circuitry 33 compresses pre-compression data, that is, projection data before compression outputted from the DAS 24 to reduce the amount of data. Specifically, the compression circuitry 33 generates compressed data containing: grouped data generated by grouping a plurality of pieces of pre-compression data; and data for restoration for restoring each piece of pre-compression data from the grouped data. The transmission circuitry 32 of the scanner apparatus 11 includes a processor, and transmits the generated compressed data to the image processing apparatus 12. The transmission circuitry 32 may transmit the grouped data and the data for restoration separately from each other.

The image processing apparatus 12 of the X-ray CT apparatus 10 includes the transmission circuitry 32, restoration circuitry 400, an image reconstructing function 410, the input circuitry 41, and the display 42. Of these components, the restoration circuitry 400 and the image reconstructing function 410 are functions implemented by executing programs stored in the memory circuitry 44 by the processing circuitry 45 including the processor.

The transmission circuitry 32 of the image processing apparatus 12 includes a processor, receives the compressed data transmitted from the compression circuitry 33, and transmits the received compressed data to the restoration circuitry 400. In addition to a scan plan and the like, a first reconstruction mode and a second reconstruction mode are selectably set to the input circuitry 41 by the user.

The first reconstruction mode is an operation mode in which image reconstruction is performed using a plurality of pieces of pre-compression data, and the second reconstruction mode is an operation mode in which image reconstruction is performed using grouped data. As described later, grouped data is generated as one piece of grouped data (integrated data) by grouping (integrating) a plurality of (for example, four) pieces of pre-compression data. Accordingly, an image with higher resolution can be generated in the first reconstruction mode in which image reconstruction is performed using a plurality of pieces of pre-compression data than in the second reconstruction mode in which image reconstruction is performed using grouped data. Meanwhile, the number of pieces of data for image reconstruction is larger in the first reconstruction mode than in the second reconstruction mode, and hence processing time required for the image reconstruction is longer in the first reconstruction mode than in the second reconstruction mode.

In a case where the first reconstruction mode is set, that is, where the image reconstructing function 410 reconstructs an image in the first reconstruction mode, the restoration circuitry 400 restores pre-compression data from compressed data using grouped data and data for restoration generated by the compression circuitry 33. The image reconstructing function 410 reconstructs the image using the restored pre-compression data.

In a case where the second reconstruction mode is set, that is, where the image reconstructing function 410 reconstructs an image in the second reconstruction mode, the restoration circuitry 400 extracts grouped data contained in compressed data, and transmits the extracted grouped data to the image reconstructing function 410. The image reconstructing function 410 reconstructs the image using the extracted grouped data.

The compression process by the compression circuitry 33 and the restoration process by the restoration circuitry 400 are more specifically described below.

Figure 3:
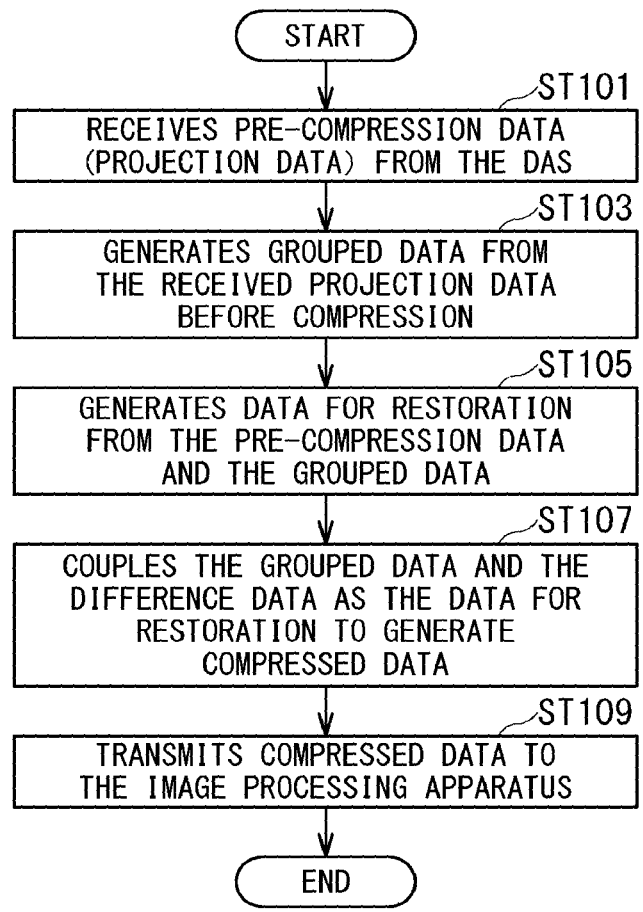
FIG. 3 is a flowchart illustrating an example of the compression process by the X-ray CT apparatus according to the first embodiment.

FIG. 3 is a flowchart illustrating an example of the compression process by the X-ray CT apparatus 10 according to the first embodiment.

In ST101, the compression circuitry 33 receives pre-compression data, that is, projection data before compression from the DAS 24. Each piece of pre-compression data corresponds one to one to an output from each X-ray detecting element of the X-ray detector 23. Accordingly, the number of the pieces of pre-compression data corresponds to the number of the X-ray detecting elements constituting the X-ray detector 23.

In ST103, the grouped data generating function 331 of the compression circuitry 33 generates grouped data from the received projection data before compression.

Figure 4:
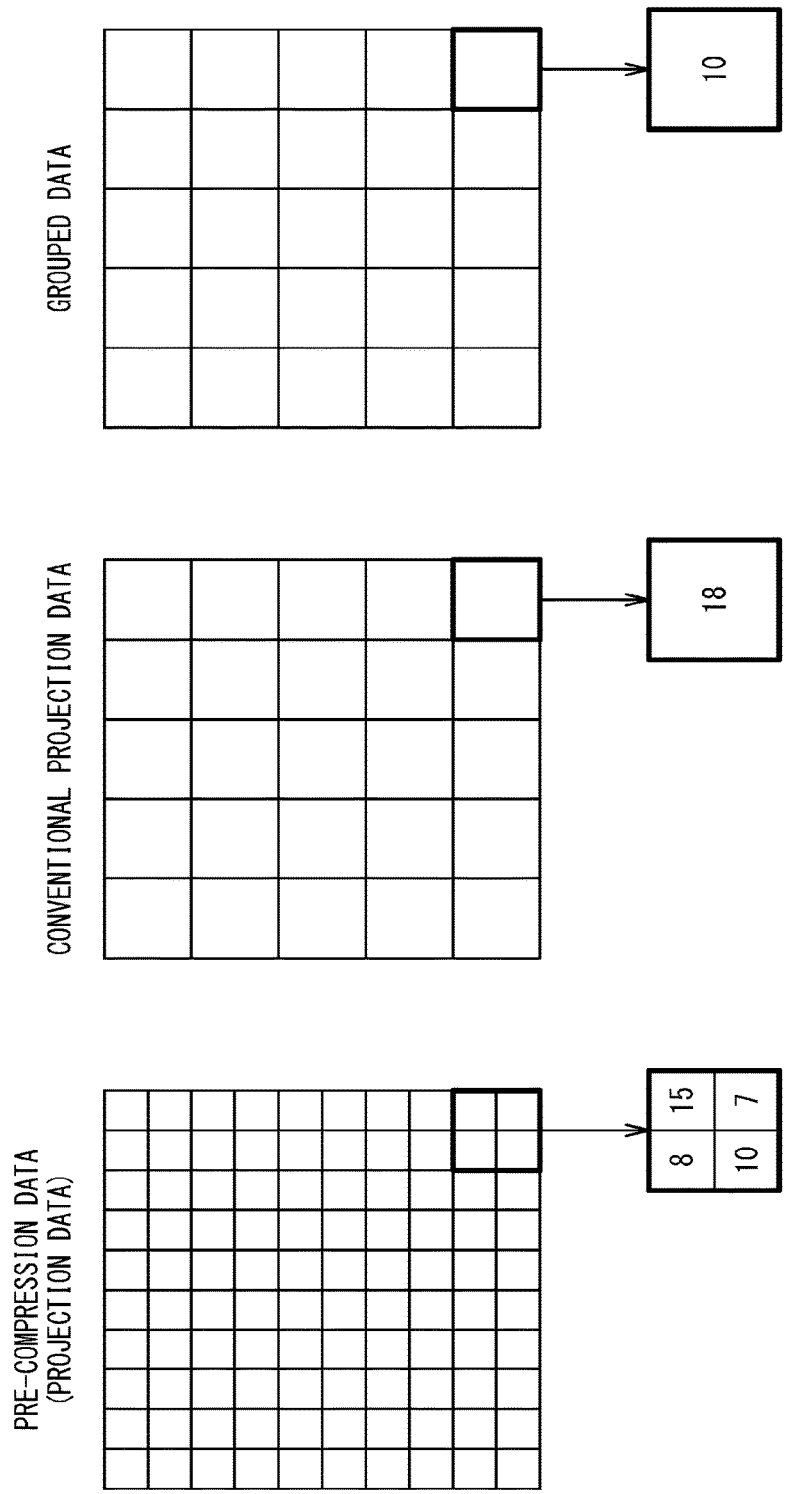
FIGS. 4A-4C are diagrams for describing an example of a method of generating the grouped data from the projection data before compression.

FIGS. 4A-4C are diagrams for describing an example of a method of generating the grouped data from the projection data before compression. FIG. 4A illustrates an example of the pre-compression data, that is, the projection data before compression acquired by the X-ray detector 23 of the present embodiment. FIG. 4B illustrates an example of projection data acquired by a conventional X-ray detector. In all of FIG. 4A to FIG. 4C, for example, a lateral direction corresponds to the channel direction, and a longitudinal direction corresponds to the slice direction. In FIG. 4A to FIG. 4C, the pieces of pre-compression data respectively corresponding to the outputs from the X-ray detecting elements are arranged in a matrix pattern in the channel direction and the slice direction. For example, the pieces of pre-compression data are arranged in a square matrix pattern with the same numbers of rows and columns in the channel direction and the slice direction.

As described above, the X-ray detector 23 of the present embodiment includes a larger number of the X-ray detecting elements in the CH direction and the slice direction than the conventional X-ray detector. Moreover, each X-ray detecting element of the X-ray detector 23 of the present embodiment is smaller in size than that of the conventional X-ray detector, and the number of the X-ray detecting elements in the same detection area is larger in the X-ray detector 23 than in the conventional X-ray detector. Hence, the number of pieces of projection data before compression acquired by the X-ray detector 23 of the present embodiment is larger than the number of pieces of projection data acquired by the conventional X-ray detector. In the examples illustrated in FIG. 4A and FIG. 4B, the number of pieces of projection data before compression acquired by the X-ray detector 23 of the present embodiment is four times the number of pieces of projection data acquired by the conventional X-ray detector. Accordingly, in the present embodiment, the number of pieces of data is reduced by compressing the acquired projection data before compression.

Specifically, the number of pieces (transmission volume) of data is reduced by grouping a plurality of pieces of pre-compression data and thus generating one piece of grouped data. In the examples illustrated in FIG. 4A and FIG. 4C, one piece of grouped data is generated by grouping, for example, four pieces of compressed data in a 2☐2 square matrix from the large number of pieces of pre-compression data arranged in a matrix pattern. As a result, for example, the number of pieces of pre-compression data that is 100 in FIG. 4A is reduced to the number of pieces of grouped data that is 25 in FIG. 4C. Namely, the number of pieces of data is reduced to one fourth.

In the examples illustrated in FIG. 4A and FIG. 4C, an averaging process of averaging CT values is used as the grouping method. A range surrounded by a thick square in a lower right of FIG. 4A includes pieces of pre-compression data respectively indicating four CT values of "8", "15", "10", and "7" in order from its upper left. Grouped data holds "10" obtained by averaging the four CT values of these pieces of pre-compression data, as a CT value of the grouped data. In this way, the number of pieces of projection data outputted from the DAS is reduced and the amount of data is reduced by averaging and grouping a plurality of pieces of pre-compression data.

Although description is given above of the example case of compressing projection data by averaging CT values, the compression method is not limited to the above-mentioned simple averaging process and may be a weighted mean process. Any other methods such as a coding process and a statistical process may be adopted as long as a plurality of pieces of pre-compression data can be integrated into one piece of grouped data.

Returning to FIG. 3, in ST105, the data-for-restoration generating function 332 generates data for restoration from the pre-compression data and the grouped data. Here, the data for restoration refers to data for restoring each piece of pre-compression data from grouped data. An example of the data for restoration is difference data. The difference data represents a difference between grouped data and each of a plurality of pieces of pre-compression data.

Figure 5:
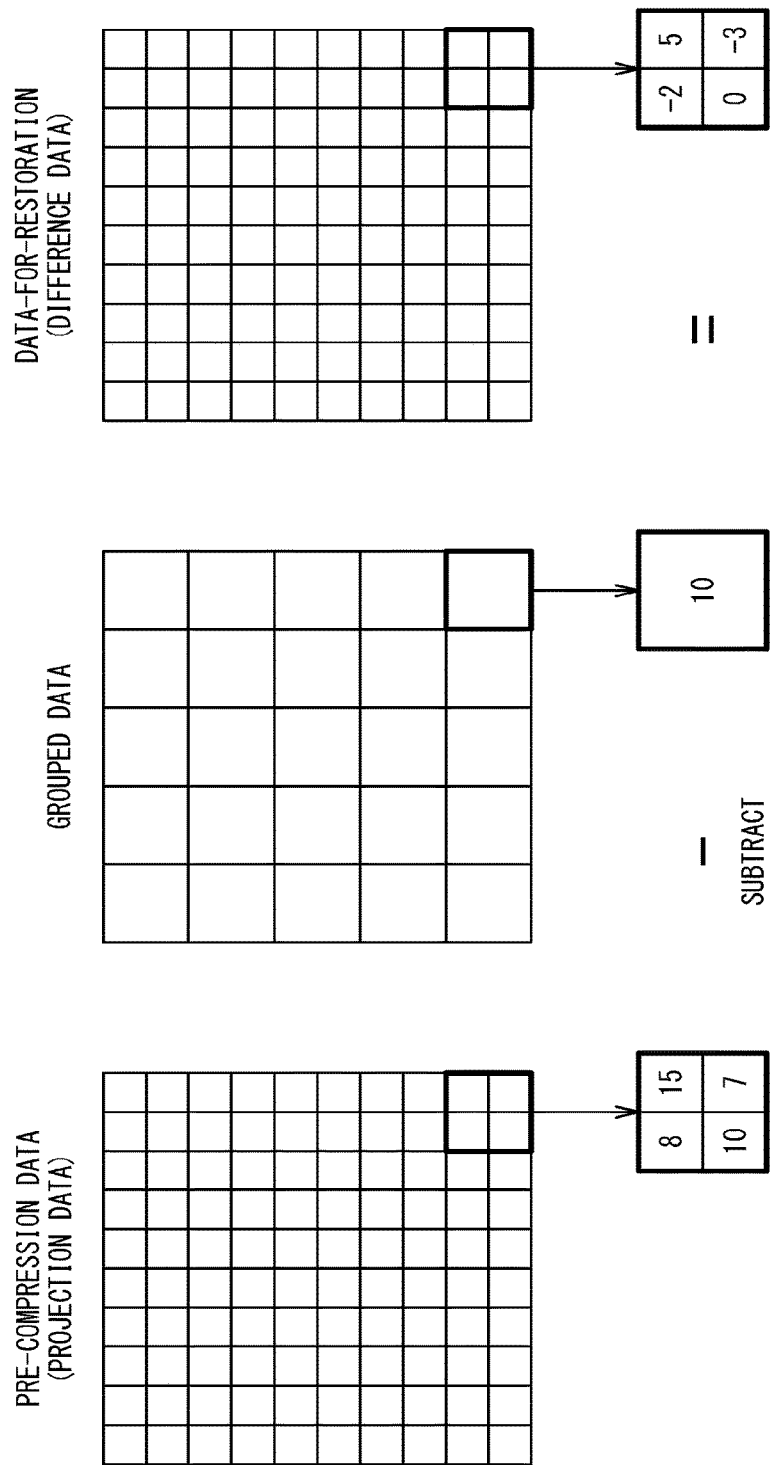
FIG. 5 is a diagram for describing a method of generating the difference data

FIG. 5 is a diagram for describing a method of generating the difference data. A left portion of FIG. 5 illustrates the same example as the pre-compression data in FIG. 4A. Similarly, a center portion of FIG. 5 illustrates the same example as the grouped data in FIG. 4C. The difference data is obtained by subtracting one piece of grouped data from each of a plurality of pieces of pre-compression data used to generate the grouped data. For example, data obtained by subtracting grouped data "10" from each of four pieces of data ("8", "15", "10", and "7") in a range surrounded by a thick square in a lower right of the pre-compression data illustrated in the left portion of FIG. 5 is calculated as the difference data. That is "−2", "5", "0", and "−3" illustrated in a lower right in a right portion of FIG. 5 are calculated as the difference data.

Returning to FIG. 3, in ST107, the data coupling function 333 couples the grouped data and the difference data as the data for restoration to generate compressed data. The compressed data is data containing: supplementary information containing information concerning generation of the compressed data; grouped data; and difference data. The supplementary information contains, for example: the number of pieces of pre-compression data corresponding to one piece of grouped data; pre-compression data volume; grouped data volume; and difference data volume. The compressed data may be generated as serialized binary data or XML data, and may be generated in a data format compliant with a format of Digital Imaging and Communication in Medicine (DICOM).

In ST109, the compressed data generated by coupling the grouped data and the difference data is transmitted to the image processing apparatus 12 via the transmission circuitry 32.

Figure 6:
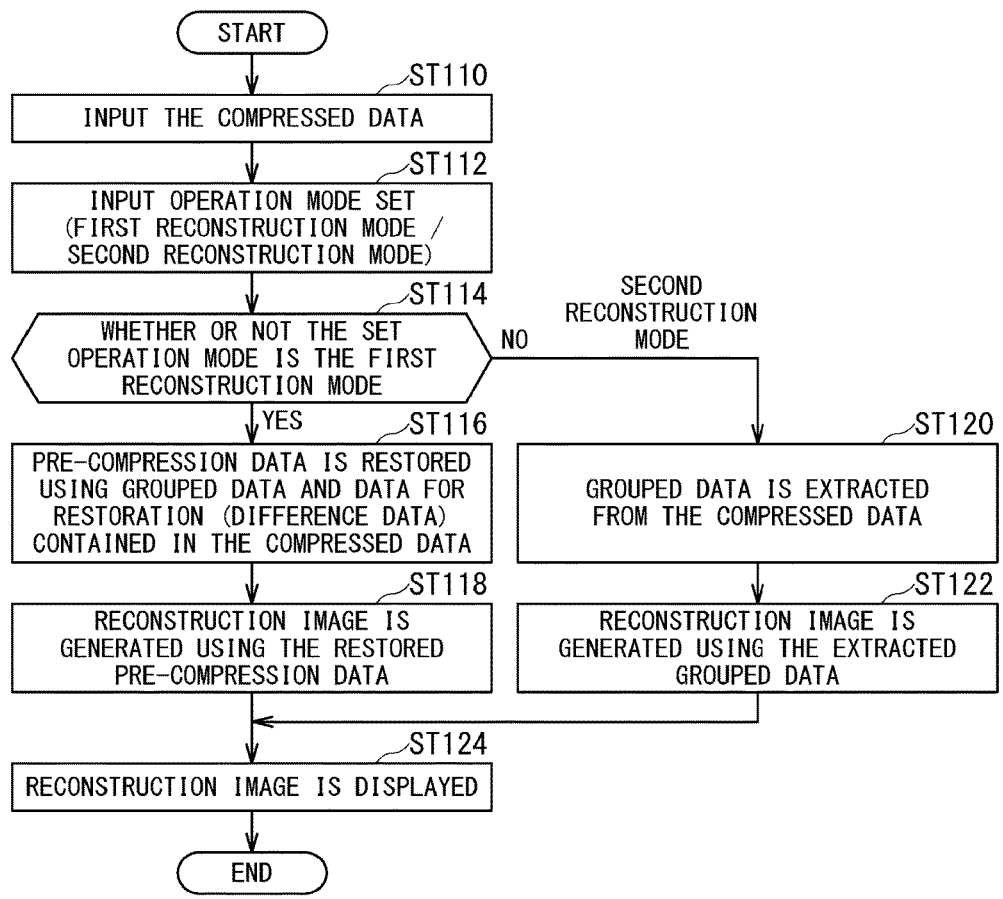
FIG. 6 is a flowchart illustrating an example of the compression process by the X-ray CT apparatus according to the first embodiment.

Next, the process of restoring and reconstructing compressed data by the image processing apparatus 12 is described with reference to a flowchart of FIG. 6.

First, in ST110, the compressed data transmitted from the compression circuitry 33 is received. In ST112, information indicating whether an operation mode set via the input circuitry 41 is the first reconstruction mode or the second reconstruction mode is received.

In ST114, it is determined whether or not the set operation mode is the first reconstruction mode. If the set operation mode is the first reconstruction mode, pre-compression data is restored using grouped data and data for restoration (difference data) contained in the compressed data (ST116).

Specifically, the grouped data is extracted from the compressed data while the plurality of (for example, four) pieces of difference data corresponding to the extracted grouped data is extracted. Then, the extracted grouped data and each of the extracted four pieces of difference data are added, whereby four pieces of pre-compression data are restored from one piece of grouped data. Such a restoration process is performed on every grouped data contained in the compressed data.

In ST118, a reconstruction image is generated using the restored pre-compression data. The generation of the reconstruction image is performed by the image reconstructing function 410.

On the other hand, if it is determined in ST114 that the set operation mode is not the first reconstruction mode, that is, is the second reconstruction mode, the process goes to ST120. In ST120, grouped data is extracted from the compressed data. Then, in ST122, a reconstruction image is generated using the extracted grouped data. The generation of the reconstruction image is also performed by the image reconstructing function 410.

Lastly, in ST124, the reconstruction image reconstructed in any of the first reconstruction mode and the second reconstruction mode is displayed on the display 42.

Although description is given above of the example case of transmitting the compressed data generated by coupling the grouped data and the data for restoration, Step of ST107 may be omitted, and the grouped data and the data for restoration may be transmitted separately from each other. For example, the grouped data is first transmitted and reconstructed into a CT image with low resolution. The data for restoration is transmitted in a background after the transmission of the grouped data. If the grouped data and the data for restoration are transmitted separately from each other in this way, throughput in transmission is further enhanced.

As described above, the X-ray detector 23 of the present embodiment includes a larger number of the X-ray detecting elements in the CH direction and the slice direction than the conventional X-ray detector, and each piece of pre-compression data corresponds one to one to an output from each X-ray detecting element. Accordingly, in the first reconstruction mode in which pre-compression data is restored from grouped data and image reconstruction is performed using the restored pre-compression data, an image can be generated with resolution higher than that of a reconstruction image generated using projection data outputted from the conventional X-ray detector. However, the number of pieces of pre-compression data used in the reconstruction process in the first reconstruction mode is larger than the number of pieces of projection data used in the conventional process, and hence the reconstruction process takes more time.

Meanwhile, in the second reconstruction mode, a smaller number of pieces of grouped data than the number of pieces of pre-compression data are used. Hence, the time required for the reconstruction process is shortened, and, for example, the reconstruction process can be performed in real time. However, in the second reconstruction mode, resolution is equivalent to that of a reconstruction image generated using projection data outputted from the conventional X-ray detector. In this way, in the present embodiment, processes respectively corresponding to the first reconstruction mode and the second reconstruction mode can be performed, and this enables flexible processing.

Whichever of the first reconstruction mode and the second reconstruction mode is selected, compressed data transmitted from the scanner apparatus 11 to the image processing apparatus 12 is data whose amount has been reduced by the compression circuitry 33, and hence the time required to transmit the compressed data is shortened. Moreover, a capacity of a memory (not illustrated) that temporarily stores the compressed data can be reduced.

Although the above description is based on an assumption that the compression circuitry 33 acquires pre-compression data from the DAS 24 through the sequential transfer process, compressed data can be generated and restored according to similar procedures even in a case of acquiring the pre-compression data through the collective transfer process.

Figure 7A:
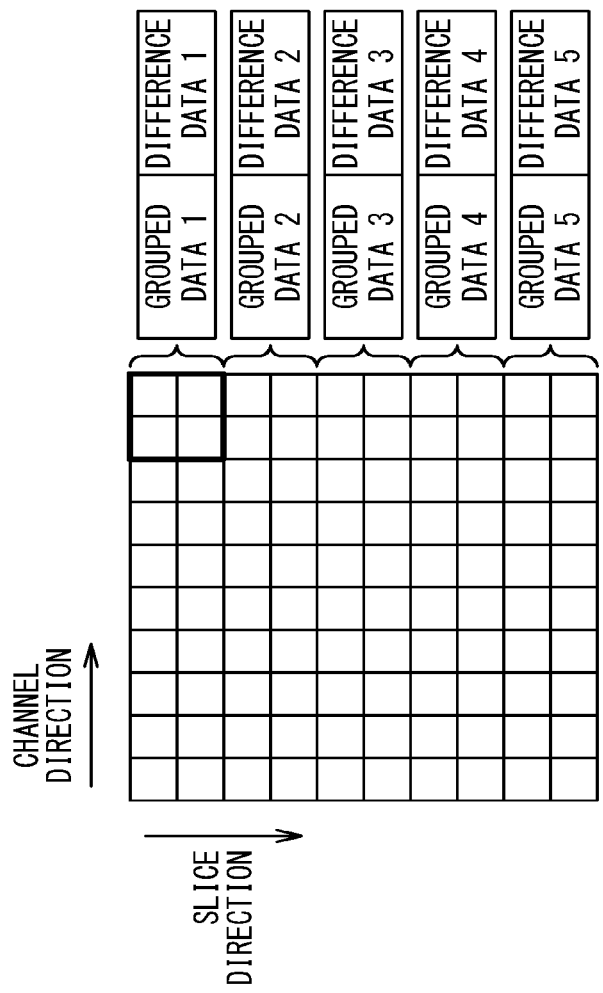
FIGS. 7A and 7B are diagrams for describing a method of generating compressed data in a case of performing the collective transfer process.
Figure 7B:

FIGS. 7A and 7B are diagrams for describing a method of generating compressed data in a case of performing the collective transfer process. In the collective transfer process, pre-compression data is outputted from the DAS 24 for each slice. FIG. 7A illustrates the same example as the pre-compression data in FIG. 4A. In order to generate grouped data having resolution in the slice direction equivalent to that of the conventional projection data illustrated in FIG. 4B, data corresponding to two rows in the slice direction of the pre-compression data illustrated in FIG. 7A is necessary. Accordingly, in a case of the sequential transfer process, the compression process is executed at timing at which pre-compression data corresponding to at least two rows is received from the DAS 24.

That is, as illustrated in FIG. 7A, the compression process is executed every two rows, so that grouped data and difference data are generated. The pieces of data thus generated are coupled in order by the data coupling function 333 with supplementary information being added as a header as illustrated in FIG. 7B, so that compressed data is generated. Coupling order in the compressed data, that is, information indicating at which position which data is coupled can be attached to the supplementary information, and hence the coupling order in the compressed data is not limited to the example illustrated in FIG. 7B. Alternatively, pieces of grouped data 1 to 5 and pieces of difference data 1 to 5 illustrated in FIG. 7A may be respectively integrated into one piece of grouped data and one piece of difference data. That is, compressed data in the same format as that in the sequential transfer process described with reference to FIG. 5 may be generated from data generated every two rows in the collective transfer process.

With regard to timing at which data is transmitted from the compression circuitry 33 to the restoration circuitry 400 of the image processing apparatus 12, for example, two transmission methods are conceivable. The first transmission method is a method of sequentially transmitting compressed grouped data to the restoration circuitry 400 at the same time as the compression process is executed. The second transmission method is a method of: storing grouped data into, for example, a memory provided in the compression circuitry 33 each time the compression process is executed; and collectively transmitting all pieces of grouped data to the restoration circuitry 400 after the compression process is executed for every pre-compression data.

In this way, the X-ray CT apparatus 10 according to the first embodiment can omit the restoration process by generating in advance grouped data compatible with conventional projection data at the time of compression, even in a case of acquiring high-definition data (pre-compression data). The number of pieces of pre-compression data grouped into grouped data (hereinafter, referred to as the grouping number) can be obtained from a ratio of the resolution of the pre-compression data and the resolution of the conventional projection data. For example, in a case where the resolution of the pre-compression data is four times the resolution of the conventional projection data as illustrated in FIG. 4A and FIG. 4B, the grouping number is set to 4. This makes the resolution of the grouped data equal to the resolution of the conventional projection data, so that the grouped data and the conventional projection data can be made compatible with each other.

In the first embodiment, the grouping number can also be determined by an index other than the ratio of the resolution of the pre-compression data and the resolution of the conventional projection data, for example, image quality such as resolution set via the input circuitry 41. For example, in a case where the resolution of the pre-compression data determined depending on the number of X-ray detecting elements is "1000☐1000", the grouping number may be determined such that the resolution becomes "500☐500", and may be determined such that the resolution becomes "100☐100". The resolution of the grouped data may be set as a ratio to the resolution of the pre-compression data such as "0.5" or "0.1". The resolution of the grouped data may be set as a magnification ratio of resolution to the conventional projection data. Such resolution settings may be stored in the memory or the like provided in the compression circuitry 33, and the compression circuitry 33 may change the grouping number in accordance with the resolution stored in the memory or the like to generate the grouped data.

Image quality settings may be determined by analyzing image quality inputted by the user or the like, a magnification ratio frequently used by the user or the like, image display settings, and the like. For example, in a case where a whole image is first observed at a low magnification ratio and where details thereof are then observed at an increased magnification ratio, the image is once displayed by performing the reconstruction process at high speed using grouped data with low resolution. After that, while the user observes the displayed image, pre-compression data with higher resolution is restored and reconstructed in a background. At the time of observation with higher resolution, the displayed image may be switched to an image reconstructed from the pre-compression data.

In this way, the X-ray CT apparatus 10 according to the first embodiment generates in advance grouped data that makes the reconstruction process efficient, at the time of compressing pre-compression data, and thus can reduce transmission volume of the pre-compression data and can shorten the time required to restore and display a reconstruction image.

Second Embodiment

In the second embodiment, difference data generated at the time of generating compressed data is further compressed.

Figure 8:
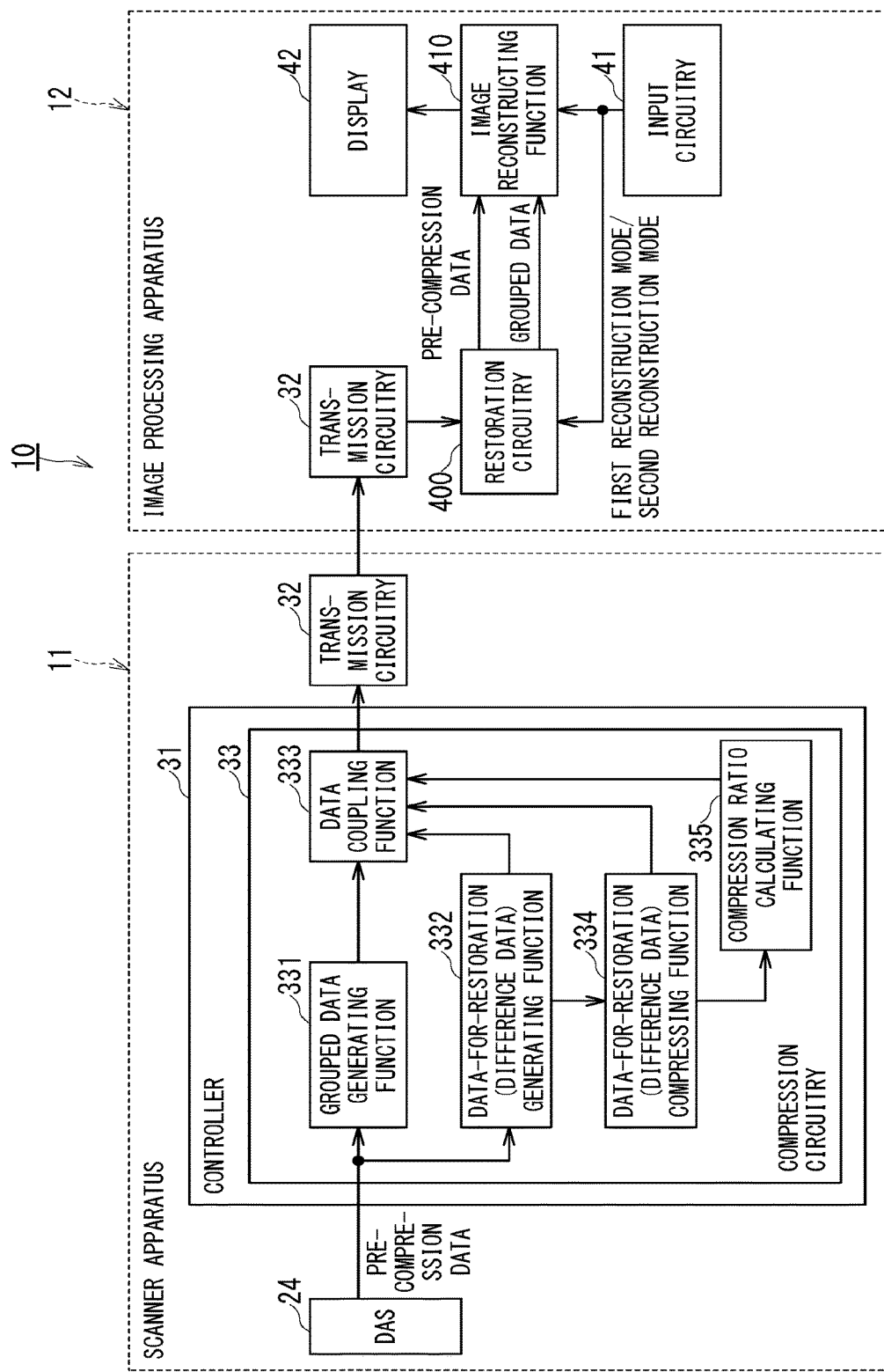
FIG. 8 is a functional block diagram illustrating a functional configuration example of the X-ray CT apparatus according to the second embodiment

FIG. 8 is a functional block diagram illustrating a functional configuration example of the X-ray CT apparatus 10 according to the second embodiment. The same configurations as those in the first embodiment illustrated in FIG. 2 are denoted by the same reference numerals, and description thereof is omitted.

As illustrated in FIG. 8, the compression circuitry 33 of the X-ray CT apparatus 10 according to the second embodiment includes a data-for-restoration (difference data) compressing function 334 and a compression ratio calculating function 335 in addition to the functions in the first embodiment. The data-for-restoration (difference data) compressing function 334 compresses difference data as data for restoration to generate compressed difference data. The difference data is compressed using, for example, a known compression algorithm.

The compression ratio calculating function 335 calculates a compression ratio of the compressed difference data. The compression ratio is calculated by, for example, obtaining a data volume ratio of difference data before compression and compressed difference data after compression.

Figure 9:
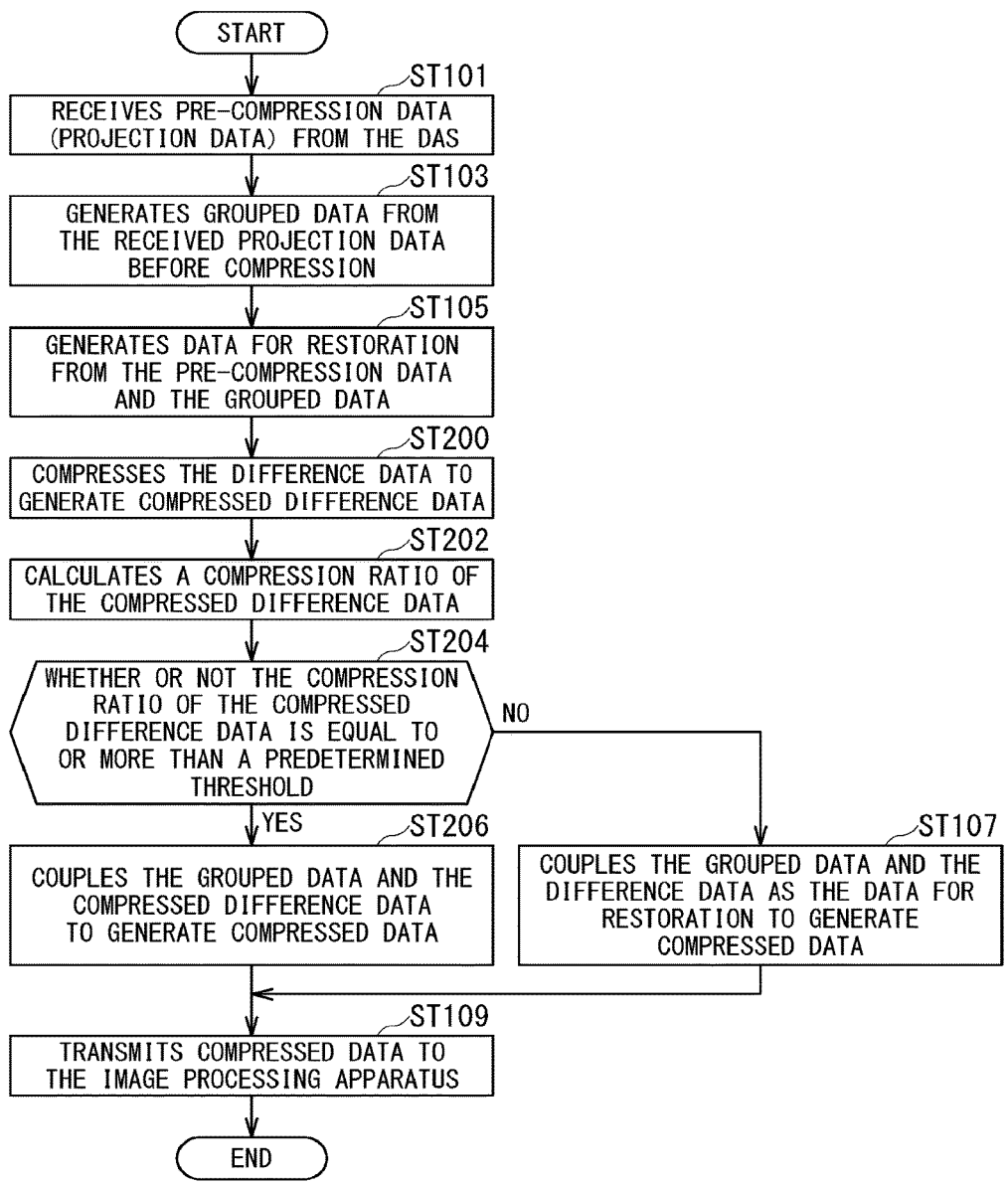
FIG. 9 is a flowchart illustrating an example of the compression process by the X-ray CT apparatus according to the second embodiment

FIG. 9 is a flowchart illustrating an example of the compression process by the X-ray CT apparatus 10 according to the second embodiment. The same steps as those in the first embodiment illustrated in FIG. 3 are denoted by the same reference signs, and description thereof is omitted.

In ST200, the data-for-restoration (difference data) compressing function 334 compresses the difference data to generate compressed difference data.

In ST202, the compression ratio calculating function 335 calculates a compression ratio of the compressed difference data.

In ST204, the data coupling function 333 determines whether or not the compression ratio of the compressed difference data is equal to or more than a predetermined threshold. If the compression ratio is equal to or more than the predetermined threshold, the data coupling function 333 couples the grouped data and the compressed difference data to generate compressed data. On the other hand, if the compression ratio is less than the predetermined threshold, the data coupling function 333 couples the grouped data and the difference data before compression to generate compressed data.

In this way, data volume can be reduced by further compressing the difference data. However, in a case where the compression ratio of the compressed difference data is small, an overhead required for restoration is more significant than an effect of such reduction in data volume by compression. In view of this, the compressed difference data is generated by once compressing the difference data, and, on a basis of the compression ratio at this time, it is determined whether the compressed data is caused to contain the compressed difference data or the difference data before compression.

Figure 10:
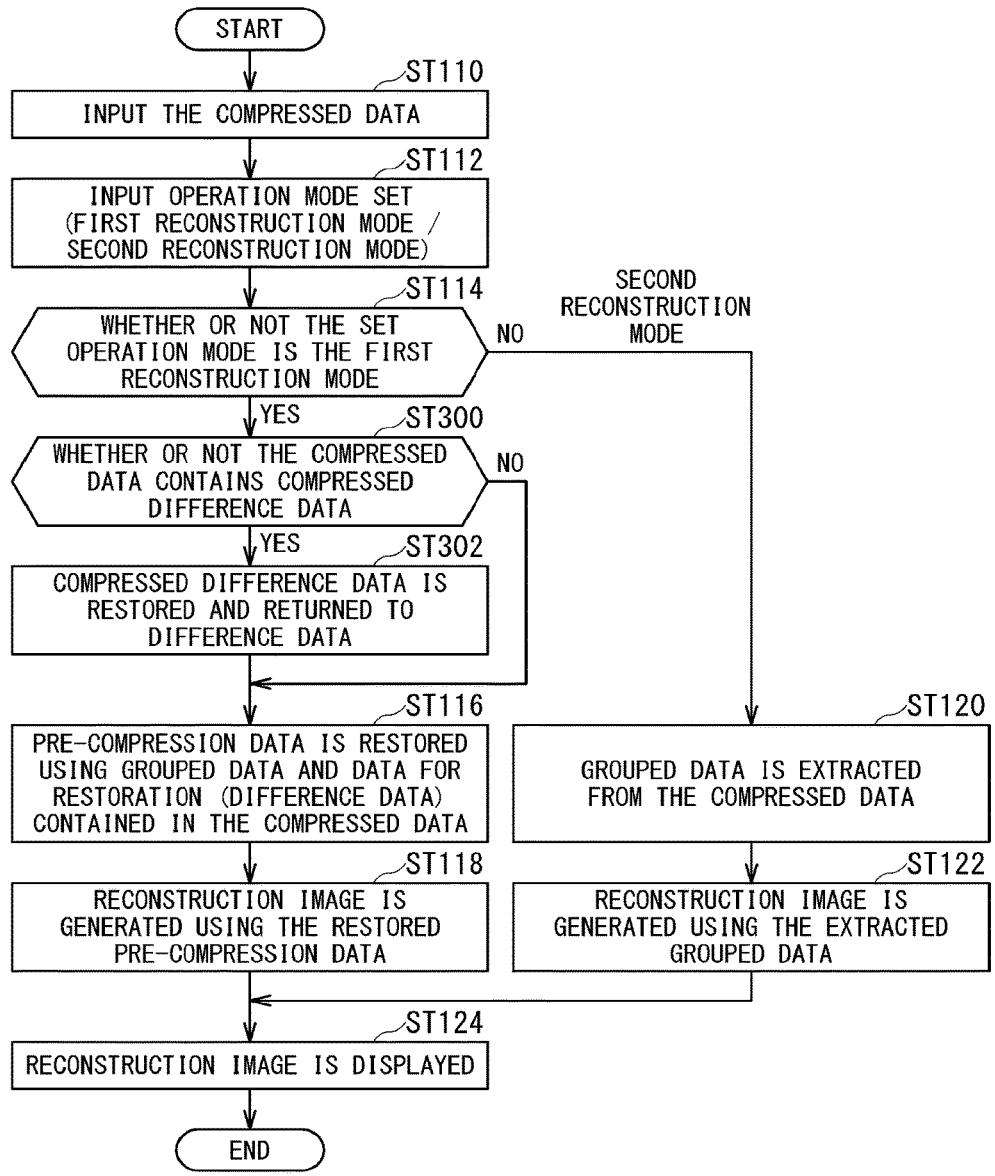
FIG. 10 is a flowchart illustrating an example of the restoration process by the X-ray CT apparatus according to the second embodiment

FIG. 10 is a flowchart illustrating an example of the restoration process by the X-ray CT apparatus 10 according to the second embodiment. The same steps as those in the first embodiment illustrated in FIG. 6 are denoted by the same reference signs, and description thereof is omitted.

In ST300, it is determined whether or not the compressed data contains compressed difference data. Whether or not the compressed data contains compressed difference data can be determined by, for example, referring to supplementary information that is caused in advance to contain information indicating whether the compressed data contains compressed difference data or difference data before compression.

If the compressed data contains compressed difference data, in ST302, the compressed difference data is restored and returned to difference data.

In the second embodiment, difference data is further compressed, and, on a basis of a compression ratio of the compressed difference data, it is determined whether to generate compressed data containing the compressed difference data and the grouped data or generate compressed data containing the grouped data and the difference data before compression. If the compression ratio of the compressed difference data is large, data volume of the generated compressed data can be reduced. On the other hand, if the compression ratio is small, the data volume cannot be reduced, and, in addition, the time required to restore the compressed difference data becomes an overhead. Accordingly, only in a case where the compression ratio is large, the compressed data is generated using the compressed difference data generated by compressing the difference data. In this way, a more efficient compression method can be selected by calculating the compression ratio, whereby an overhead in restoration at the time of image reconstruction can be reduced.

Third Embodiment

In the third embodiment, it is determined whether or not to compress collected pre-compression data, and compressed data is generated only when efficient compression is possible.

Figure 11:
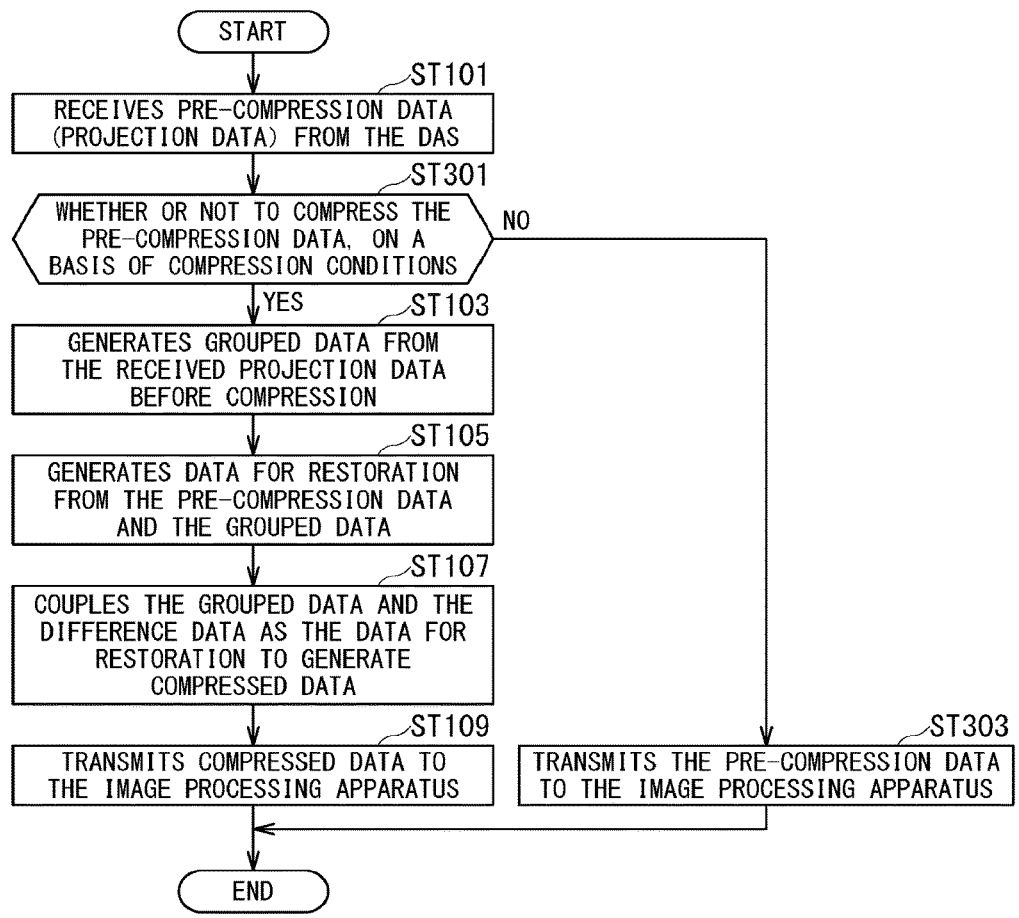
FIG. 11 is a flowchart illustrating an example of the compression process by the X-ray CT apparatus according to the third embodiment.

FIG. 11 is a flowchart illustrating an example of the compression process by the X-ray CT apparatus according to the third embodiment. The same steps as those in the first embodiment illustrated in FIG. 3 are denoted by the same reference signs, and description thereof is omitted.

In ST301, the compression circuitry 33 determines whether or not to compress the pre-compression data, on a basis of compression conditions. Examples of the compression conditions include: a condition that non-uniformity (specifically, a standard deviation, an average difference, or an average absolute deviation) of signal values in a sinogram calculated from the pre-compression data (projection data) is equal to or more than a predetermined threshold; and a condition that the signal values are equal to or more than a predetermined threshold.

In a case where the signal values in the sinogram of the pre-compression data are non-uniform, that is, where high-signal pixels and low-signal pixels mixedly exist and are adjacent to each other or scattered over all, a compression ratio at the time of generating difference data is expected to be large. Conditions for determining in advance that the compression ratio is large or the compression is effective on a basis of such signal value distribution and signal value magnitude over the entire pre-compression data are stored in advance as the compression conditions. When the pre-compression data is received, it is determined whether or not to compress the pre-compression data, on the basis of the compression conditions. If the pre-compression data is to be compressed (Yes in ST 301), the pre-compression data is compressed according to Steps from ST103 to ST109 in the first embodiment. The pre-compression data may be compressed according to the method of the second embodiment. On the other hand, if it is determined that, even if the pre-compression data is compressed, adequate compression is not expected on the basis of the compression conditions (No in ST 301), the pre-compression data is transmitted to the image processing apparatus without any change (ST303).

Although description is given above of the example case of determining the compression conditions over the entire pre-compression data and determining whether or not to compress the pre-compression data, the compression conditions may be determined on a basis of part of the pre-compression data. For example, the compression conditions may be determined using only a partial region corresponding to an object on a sinogram. Specifically, the region showing the object on the sinogram corresponds to a region with a small dose of transmitted X-rays on the sinogram. A signal value and a predetermined threshold are compared with each other, and the determination based on the compression conditions is performed on only a region for which X-ray absorption equal to or more than a given threshold can be determined.

Instead of the entire pre-compression data, such a partial region may be compressed to generate compressed data. That is, grouped data may be partially generated, and the other portion may be compressed so as to have pixels before compression or predetermined pixels. For example, only data within a predetermined channel range on a sinogram, that is, data around a center of the sinogram may be compressed, and data in a remaining peripheral region may not be compressed, whereby grouped data may be partially generated.

Compressed data mixedly containing compressed data and pre-compression data may be generated. Alternatively, only compressed data that is partially compressed may be transmitted to the image processing apparatus.

In this way, the compression process is performed in a case where the compression can be determined to be effective on the basis of the compression conditions, whereby resources can be effectively utilized. Moreover, the compression process is not performed in a case where the compression is not effective, whereby the time required for the compression and restoration can be saved.

Another Embodiment

Figure 12:
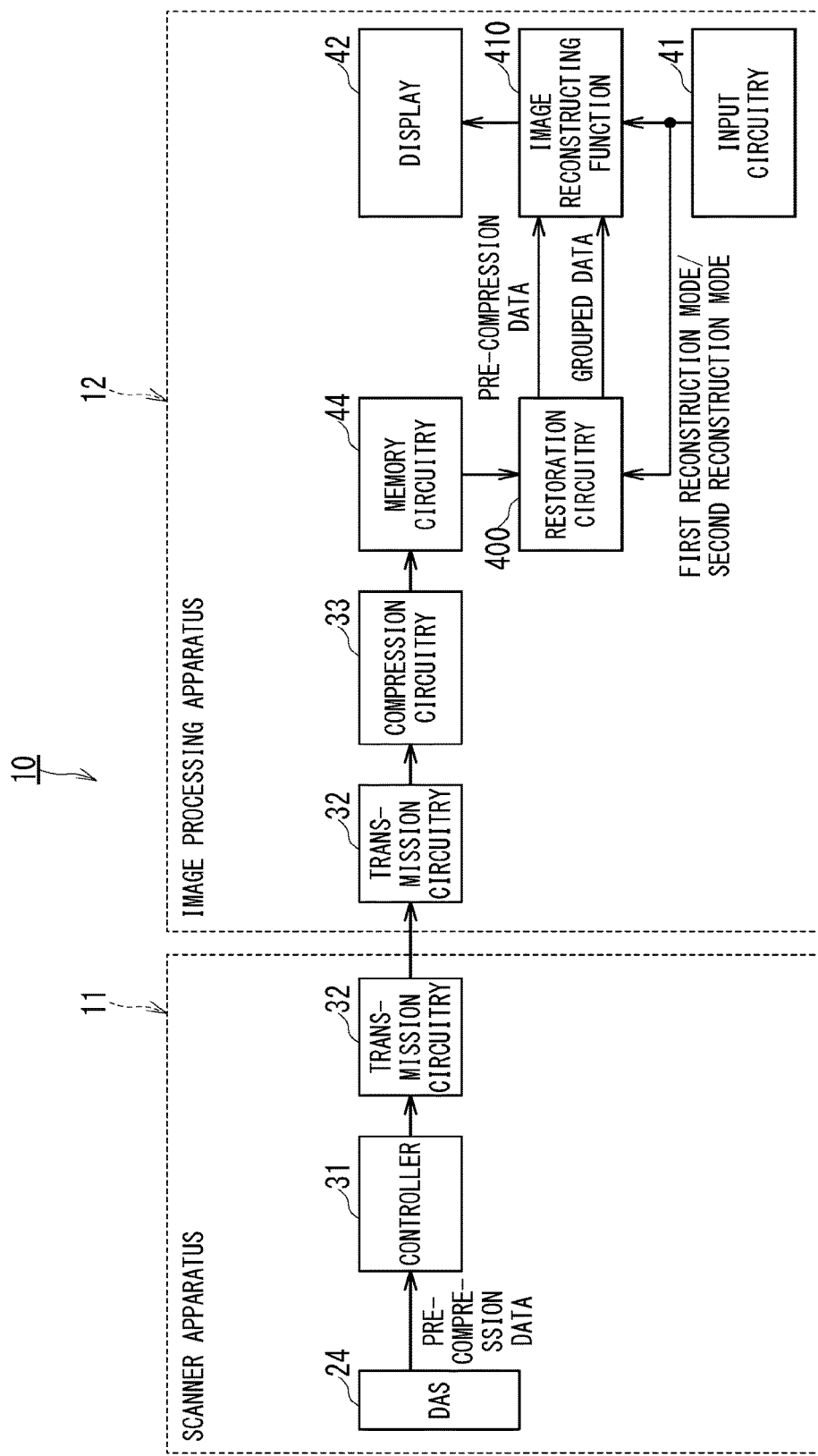
FIG. 12 is a functional block diagram illustrating this configuration example.

In the first to third embodiments, the compression circuitry 33 is provided in the scanner apparatus 11 or the frame apparatus installed in the examination room. Alternatively, the compression circuitry 33 may be provided in the image processing apparatus 12. FIG. 12 is a functional block diagram illustrating this configuration example. As illustrated in FIG. 12, pre-compression data from the DAS 24 is transmitted via the controller 31 and the transmission circuitry 32, and is compressed by the compression circuitry 33 in the image processing apparatus 12, so that compressed data containing grouped data and data for restoration (difference data) is generated. The compressed data is temporarily stored in the memory circuitry 44. The subsequent processing is the same as that in the first and second embodiments.

Also in this configuration, in the first reconstruction mode, an image can be generated with resolution higher than that of a reconstruction image generated using projection data outputted from the conventional X-ray detector. Meanwhile, in the second reconstruction mode, a smaller number of pieces of grouped data than the number of pieces of pre-compression data are used. Hence, the time required for the reconstruction process is shortened, and, for example, the reconstruction process can be performed in real time. In this way, also in another embodiment illustrated in FIG. 12, processes respectively corresponding to the first reconstruction mode and the second reconstruction mode can be performed, and this enables flexible processing. Moreover, because data stored in the memory circuitry 44 is compressed data, a memory capacity may be smaller than that in a case of storing pre-compression data without any change.

With the X-ray CT apparatus and the data compression/restoration method according to at least one embodiment described above, high-definition data acquired by a high-definition X-ray CT apparatus can be efficiently compressed in a restorable manner.

The term "processor" in the above-described embodiments means, for instance, a circuit such as a special-purpose or general-purpose CPU (Central Processing Unit), a special-purpose or general-purpose GPU (Graphics Processing Unit), an ASIC (Application Specific Integrated Circuit), a programmable logic device including an SPLD (Simple Programmable Logic Device) and a CPLD (Complex Programmable Logic Device) as examples, and an FPGA (Field Programmable Gate Array).

A processor implements various types of functions by reading out programs stored in a memory circuit and executing the programs.

In addition, programs may be directly installed in the circuit of the processor instead of storing the programs in a separate memory circuit. In this case, the processor implements various types of functions by reading out programs installed in its circuit and executing these programs.

Although a case where unified processing circuitry implements respective functions has been described in the above-described embodiments, the processing circuitry may be configured by combining plural processors being independent of each other so that each of the processers implements each function by executing the corresponding program.

Furthermore, when plural processors are provided, memory media for storing programs may be provided for the respective processors or one memory medium may collectively store all the programs corresponding to the functions of each processor.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:
1. An X-ray CT apparatus, comprising:
an X-ray source configured to radiate an X-ray;
a detector configured to output a piece of first data corresponding to a first resolution based on detecting the X-ray;
first processing circuitry; and
second processing circuitry, wherein
the first processing circuitry is configured to
integrate pieces of the first data
generate a piece of second data corresponding to the pieces of the first data, the piece of the second data corresponding to a second resolution lower than the first resolution, generate restoration data for restoring the pieces of the first data by taking a difference between each of the pieces of the first data and the piece of the second data, and transmit the piece of the second data and the restoration data to the second processing circuitry, and the second processing circuitry is configured to select any of: a first reconstruction mode in which image reconstruction is performed based on the pieces of the first data; and a second reconstruction mode in which image reconstruction is performed based on the piece of the second data, and (A) restore the pieces of the first data based on the transmitted piece of the second data and the restoration data, and generate a higher resolution image based on the restored pieces of the first data when the first reconstruction mode is selected, and (B) generate a lower resolution image based on the transmitted piece of the second data when the second reconstruction mode is selected.

2. The X-ray CT apparatus according to claim 1, wherein the detector includes X ray detecting elements, and the pieces of the first data are respectively outputted from the X ray detecting elements.

3. The X-ray CT apparatus according to claim 1, wherein the first processing circuitry is configured to integrate a different number of pieces of the first data in accordance with image quality in the second reconstruction mode.

4. The X-ray CT apparatus according to claim 1, wherein the first processing circuitry is configured to integrate the pieces of the first data in a square matrix with a same number of rows and columns in a slice direction and a channel direction, respectively, to generate the piece of the second data.

5. The X-ray CT apparatus according to claim 1, wherein the piece of the second data generated by the first processing circuitry is data generated by performing at least any of an averaging process, a coding process, and a statistical process on the pieces of the first data, the piece of the second data having a smaller data amount than the integrated pieces of the first data.

6. The X-ray CT apparatus according to claim 1, further comprising input circuitry configured to selectively receive any operation mode of the first reconstruction mode and the second reconstruction mode, wherein the second processing circuitry is configured to select whether to perform image reconstruction in the first reconstruction mode using the pieces of the first data or perform image reconstruction in the second reconstruction mode using the piece of the second data, in accordance with the received operation mode.

7. The X-ray CT apparatus according to claim 1, wherein the first processing circuitry is further configured to compress the difference data, defined as the difference between each of the pieces of the first data and the piece of the second data, and the second processing circuitry is configured to restore, in the case of performing the image reconstruction in the first reconstruction mode, the compressed difference data, and restore the pieces of the pieces of the first data using the restored difference data and the piece of the second data.

8. The X-ray CT apparatus according to claim 7, wherein the first processing circuitry is configured to obtain a compression ratio of the compressed difference data to the difference data; and generate, when the compression ratio is more than a predetermined threshold, the compressed difference data and the piece of the second data, and generate, when the compression ratio is equal to or less than the predetermined threshold, the difference data before compression and the piece of the second data, and the second processing circuitry is configured to restore, when the compression ratio is more than the predetermined threshold, the pieces of the first data using the restored difference data and the piece of the second data, and restore when the compression ratio is equal to or less than the predetermined threshold, the pieces of the first data using the difference data before compression and the piece of the second data.

9. The X-ray CT apparatus according to claim 1, wherein the first processing circuitry is configured to determine whether or not to compress the pieces of the first data, based on a compression condition.

10. The X-ray CT apparatus according to claim 1, wherein the first processing circuitry is further configured to determine whether or not to compress the pieces of the first data, in accordance with a variance in sinogram data generated from the pieces of the first data.

11. A data compression/restoration method, comprising:

outputting a piece of first data corresponding to a first resolution based on data from a detector resulting from detecting an X-ray radiated by an X-ray tube;

integrating pieces of pre the first data;

generating a piece of second data corresponding to the pieces of the first data, the piece of the second data corresponding to a second resolution lower than the first resolution;

generating restoration data for restoring the pieces of the first data by taking a difference between each of the pieces of the first data and the piece of the second data;

transmitting the piece of the second data and the restoration data to an image reconstruction apparatus;

selecting any of: a first reconstruction mode in which image reconstruction is performed based on the pieces of the first data; and a second reconstruction mode in which image reconstruction is performed based on the piece of the second data; and (A) restoring the pieces of the first data based on the transmitted piece of the second data and the restoration data, and generating a higher resolution image based on the restored pieces of the first data when the first reconstruction mode is selected, and (B) generating a lower resolution image based on the transmitted piece of the second data when the second reconstruction mode is selected.

* * * * *